US008382733B2

(12) United States Patent      (10) Patent No.: US 8,382,733 B2
Okawa et al.      (45) Date of Patent: Feb. 26, 2013

(54) ABSORBENT PRODUCT

(75) Inventors: Miyuki Okawa, Mima-gun (JP); Akiko Tatsukawa, Mima-gun (JP); Hirofumi Miyake, Mima-gun (JP)

(73) Assignee: Livedo Corporation, Ehime (JP)

( * ) Notice: Subject to any disclaimer, the term of this patent is extended or adjusted under 35 U.S.C. 154(b) by 631 days.

(21) Appl. No.: 12/612,739

(22) Filed: Nov. 5, 2009

(65) Prior Publication Data

US 2010/0121294 A1     May 13, 2010

(30) Foreign Application Priority Data

Nov. 11, 2008    (JP) ................. P2008-288420

(51) Int. Cl.
     *A61F 13/15*      (2006.01)
     *A61F 13/20*      (2006.01)

(52) U.S. Cl. .............................. 604/385.101

(58) Field of Classification Search ............. 604/385.01, 604/385.03, 385.101, 385.24–385.3
See application file for complete search history.

(56) References Cited

U.S. PATENT DOCUMENTS

| 5,342,342 | A | 8/1994 | Kitaoka |
| 5,601,546 | A | 2/1997 | Tanji et al. |
| 6,248,098 | B1 | 6/2001 | Sayama |
| 2002/0099351 | A1 | 7/2002 | Onishi et al. |
| 2003/0114819 | A1 | 6/2003 | Sayama et al. |
| 2006/0173435 | A1 | 8/2006 | Nakajima et al. |
| 2009/0287177 | A1 | 11/2009 | Tatsukawa et al. |

FOREIGN PATENT DOCUMENTS

| AU | 2009201792 | 12/2009 |
| CN | 1372874 | 10/2002 |
| CN | 1426770 | 7/2003 |
| EP | 0 565 058 | 10/1993 |
| EP | 0 673 630 | 9/1995 |
| EP | 1 224 922 | 7/2002 |
| EP | 1 323 399 | 7/2003 |
| EP | 1 731 124 | 12/2006 |
| EP | 1 731 124 A1 * | 12/2006 |
| EP | 2 123 244 | 11/2009 |

(Continued)

OTHER PUBLICATIONS

European Search Report (in English language) issued Feb. 12, 2010 in corresponding European Patent Application No. 09013596.3.

(Continued)

*Primary Examiner* — Michele M Kidwell
(74) *Attorney, Agent, or Firm* — Wenderoth, Lind & Ponack, L.L.P.

(57) ABSTRACT

In an absorbent product (1), a front pocket (26) and a rear pocket (27) are formed between a front absorbent core (212) and a rear absorbent core (222) and a back sheet (23). A pair of side sheets (3) are located on both side portions of an absorbent sheet member (20) having an opening (25). Both absorbent cores are raised so that they become spaced apart from the back sheet (23) by contraction of a third elastic member (35) bonded to an inner edge (331) of a bonded part (33) of each side sheet (3). It is possible to keep the distance larger in a thickness direction between the absorbent sheet member (20) and the back sheet (23) in the vicinity of the opening (25) and fit a portion around the opening (25) of the absorbent sheet member (20) to a wearer.

14 Claims, 6 Drawing Sheets

FOREIGN PATENT DOCUMENTS

| | | |
|---|---|---|
| JP | 2-126850 | 5/1990 |
| JP | 3406205 | 5/2003 |
| JP | 3964624 | 8/2007 |
| JP | 2007-300940 | 11/2007 |

OTHER PUBLICATIONS

Australian Notice of Allowance issued Jul. 12, 2012 in corresponding Australian Application No. 2009230764.

* cited by examiner

ABSORBENT PRODUCT

BACKGROUND OF THE INVENTION

1. Field of the Invention

The present invention relates to an absorbent product for receiving excrement from a wearer.

2. Description of the Background Art

Conventionally, in a case where loose stool containing much moisture is excreted in an absorbent product such as a disposal diaper, various suggestions have been made for preventing the loose stool from expanding between a wearer and the absorbent product and adhering to the wearer in a wide range.

Japanese Patent Application Laid-Open No. 2007-300940 (Document 1) discloses a disposable wearing article where a sheet liner having an opening provided in its center and facing a wearer's anus, is positioned on a semi-rigid absorbent panel fixed on a back sheet, said liner facing a rear waist region of the absorbent panel, and loose stool which has passed through the opening in the liner is kept in a small space between the liner and the absorbent panel, to thereby prevent adhesion of the loose stool to the wearer. In Document 1, an elastic member is bonded to the liner along the peripheral edge of the opening in the liner to maintain the form of the opening, and elastic members extending in a longitudinal direction on the both sides in a width direction of the opening are bonded to the liner so that the liner should be lifted up and be spaced apart from the absorbent panel.

Japanese Patent Gazette No. 3406205 (Document 2) discloses a disposable diaper where a sheet-like top wall is provided between distal edges (i.e., both upper portions) of a pair of side walls which extend in a longitudinal direction on the both sides in a width direction, standing toward a wearer, a cavity is formed by an absorbent core, the pair of side walls, and the top wall which faces the absorbent core with a space, and the excrement which has passed through an opening provided in the top wall is kept in the cavity. In the disposable diaper of Document 2, a pad member which is preferably made of crimped synthetic fibers or a soft foam plastic sheet such as urethane foam sheet is provided around the opening in the top wall to prevent the opening in the top wall from moving the wearer's anus or the like.

In a paper diaper disclosed in Japanese Patent Application Laid-Open No. 2-126850 (Document 3), a coarse surface sheet is located between a pair of barrier cuffs which extend in a longitudinal direction on the both sides in a width direction and stands toward a wearer, the surface sheet being apart from a liquid-pervious sheet positioned on an absorbent core. Loose stool which has passed through the surface sheet is kept in a space between the surface sheet and the liquid-pervious sheet. In the paper diaper of Document 3, the standing form of the pair of barrier cuffs in wearing the paper diaper is maintained by bending the barrier cuffs toward the outside in the width direction.

In the disposable wearing article of Document 1, since the liner is a thin sheet in which two sheets are laminated, there is a possibility that the space between the liner and the absorbent panel is easily depressed by the body pressure of wearer or the like and the loose stool or the like cannot be kept in the space. Further, the liner may be twisted by the movement of wearer to move the opening from the wearer's anus or the like.

Similarly in the disposable diaper of Document 2, since the top wall (excluding a portion around the opening) is a thin sheet, there is a possibility that the cavity between the top wall and the absorbent core is easily depressed by the body pressure or the like and the loose stool or the like cannot be kept in the cavity. Further, in the disposable diaper of Document 2, the side walls and the outer surface of the top wall have hydrophobicity (preferably, hydrophobicity and liquid imperviousness). If the opening moves from the anus or the like even if only slightly, the excrement which has not passed through the opening expands onto the front and back of the disposable diaper along the top wall and adheres to the wearer widely.

Similarly in the paper diaper of Document 3, the space between the surface sheet and the liquid-pervious sheet is lost and the loose stool or the like may not be kept in the space. Further, in the paper diaper of Document 3, if the mesh size of the surface sheet is too small, loose stool or the like expands over the surface sheet without passing through the surface sheet. On the other hand, if the mesh size of the surface sheet is too large, loose stool or the like which has passed through the surface sheet returns to the outside of the surface sheet before being sufficiently absorbed into the absorbent core. In both cases, loose stool or the like adheres to the wearer in a wide range.

SUMMARY OF THE INVENTION

The present invention is intended for an absorbent product for receiving excrement from a wearer. It is an object of the present invention to keep the distance larger in a thickness direction between an absorbent sheet member and a back sheet in the vicinity of an opening and to fit a portion around the opening of the absorbent sheet member to the wearer.

The absorbent product comprises: a back sheet; an absorbent sheet member which is overlapped on the back sheet, having an opening to come into contact with a crotch region of a wearer; and a pair of side sheets located on both side portions of the absorbent sheet member, extending in a longitudinal direction of the absorbent sheet member, and in the absorbent product, the absorbent sheet member comprises: a front absorbent core to be positioned on a front side of the wearer; a rear absorbent core to be positioned on a back side of the wearer; and a liquid-pervious core covering sheet for covering the front absorbent core and the rear absorbent core, having the opening between the front absorbent core and the rear absorbent core, an outer portion of one absorbent core out of the front absorbent core and the rear absorbent core in the absorbent sheet member, excluding a portion around the opening, is bonded to the back sheet, to form a pocket between the one absorbent core and the back sheet, and each of the pair of side sheets comprises: a bonded part which is a strip-like portion bonded on the core covering sheet, an inner edge of the bonded part being located in the inside of a side edge of the opening; a side wall part, at least part of the side wall part standing up from the inner edge of the bonded part; and an elastic member which is bonded on the bonded part in the longitudinal direction inner than the side edge of the opening or bonded on the side wall part in the vicinity of the bonded part across the opening, the one absorbent core being drawn toward the other absorbent core by contraction of the elastic member. It is thereby possible to keep the distance larger in the thickness direction between the absorbent sheet member and the back sheet in the vicinity of the opening and to fit a portion around the opening of the absorbent sheet member to the wearer.

According to a preferred embodiment of the present invention, the side wall part stands up toward the outside from the inner edge of the bonded part. With this structure, since the side wall part is easily to contact the wearer along the crotch region, leakage of excrement can be surely prevented. According to another preferred embodiment of the present invention, the bonded part is not bonded with the core covering sheet in the vicinity of an edge of the opening above the one absorbent core. It is thereby possible to increase the distance in the thickness direction between the absorbent sheet member and the back sheet in the vicinity of the opening.

According to another preferred embodiment of the present invention, the absorbent sheet member further comprises other elastic members which are bonded on the core covering sheet, extending in the both side portions of the absorbent sheet member in the longitudinal direction, and other elastic members extend at least from outward positions of both side edges of the opening to positions where other elastic members overlay with the one absorbent core, and the one absorbent core is drawn toward the other absorbent core by contraction of other elastic members. Thus, it is possible to increase the distance in the thickness direction between the absorbent sheet member and the back sheet in the vicinity of the opening, similarly to the above case.

According to still another preferred embodiment of the present invention, the one absorbent core has a weakened line group located in the center with respect to a width direction of the absorbent sheet member, the weakened line group extending approximately along the longitudinal direction from a core edge of the one absorbent core, the core edge being located close to the opening or in contact with the opening, and the one absorbent core is bent at the weakened line group, to form a projected part projecting toward a wearer. With this structure, it is possible to further fit a portion around the opening of the absorbent sheet member to the wearer.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
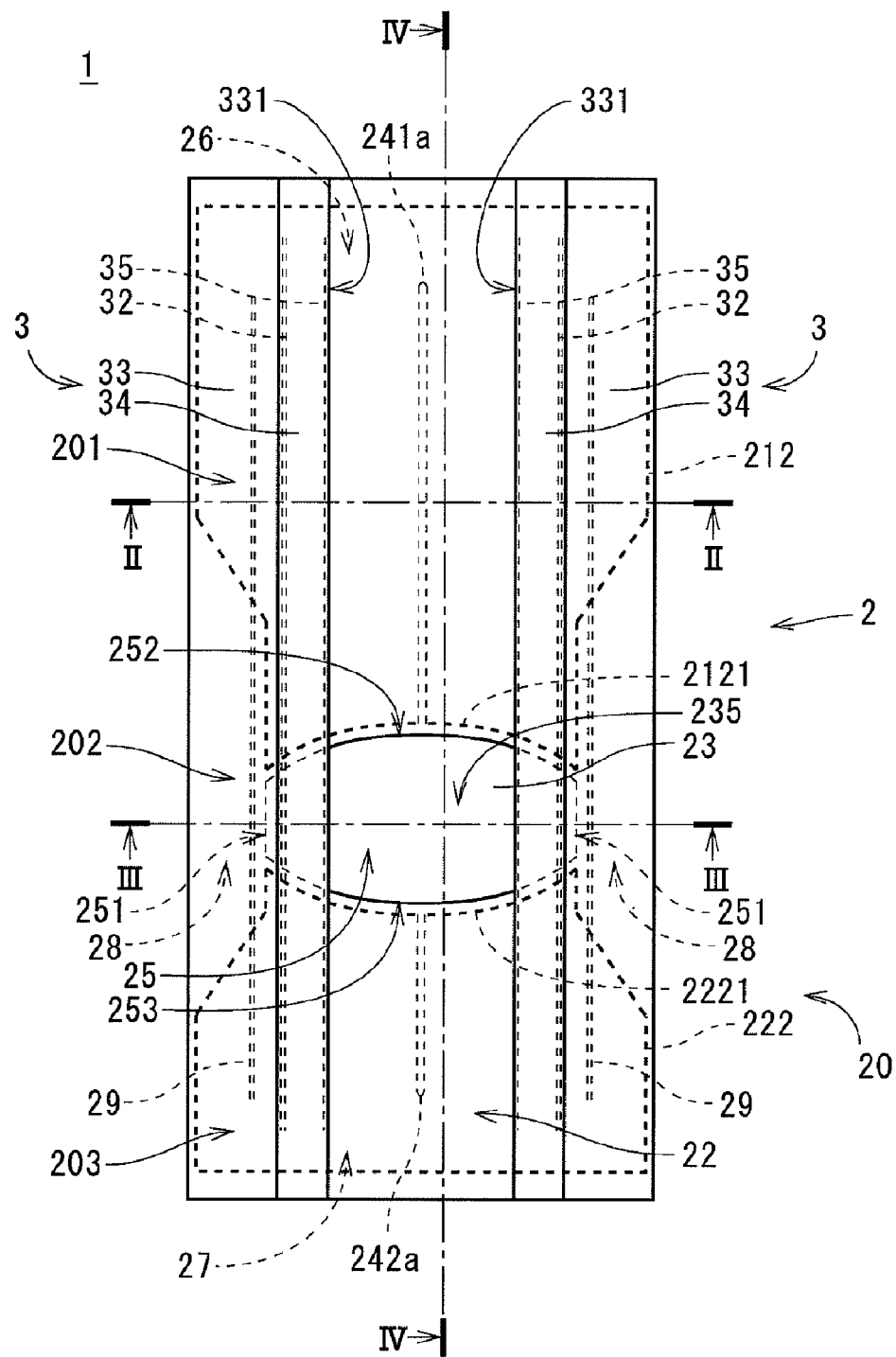
FIG. 1 is a plan view of an absorbent product.

FIG. 1 is a plan view showing an expanded absorbent product 1 in accordance with a preferred embodiment of the present invention. The absorbent product 1 is an auxiliary absorbent pad which is attached on an inner side of a disposal diaper and the like which is an exterior product worn by a wearer in order to receive excrement such as loose stool discharged from the wearer. FIG. 1 shows a surface of the absorbent product 1, which is to come into contact with the wearer's body during use.

As shown in FIG. 1, the absorbent product 1 has a sheet-like main body part 2 which is a substantially rectangle in plan view and a pair of side sheets 3 located on both side portions of the main body part 2, extending in a longitudinal direction of an absorbent sheet member 20, the longitudinal direction being perpendicular to a width direction (i.e., the both side portions are those in the width direction of the main body part 2 in FIG. 1 and are those in the width direction of the absorbent sheet member 20 discussed later). The side sheets 3 are located over almost the entire length of the main body part 2.

An upper portion 201 and a lower portion 203 of the main body part 2 in FIG. 1 are a portion to be positioned on the front side of the wearer and a portion to be positioned on the back side, respectively, and they are referred to as a "front part 201" and a "rear part 203" in the following description. A portion 202 which is continuous with the front part 201 and the rear part 203 between the front part 201 and the rear part 203 and is to come into contact with a crotch region of the wearer, is referred to as a "middle part 202".

Figure 2:
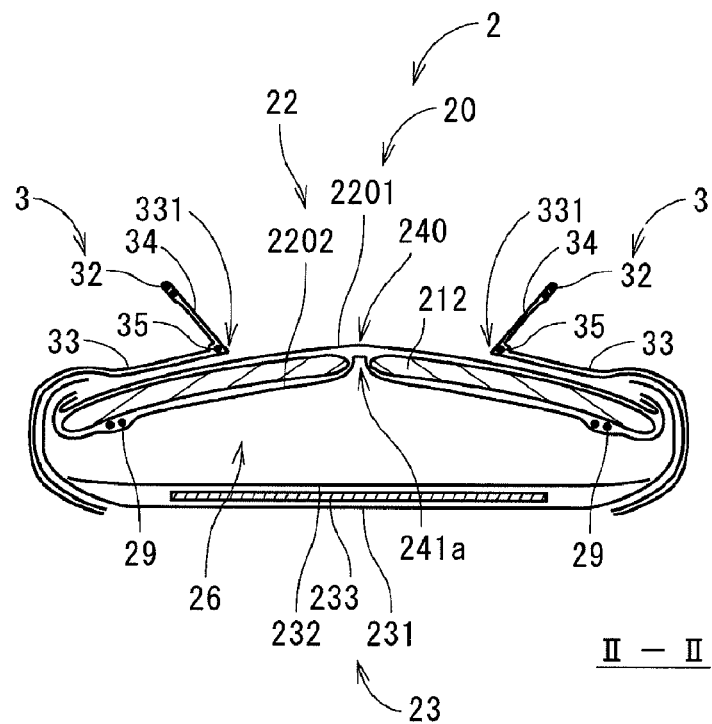
FIGS. 2, 3 and 4 are cross-sectional views of the absorbent product.
Figure 3:
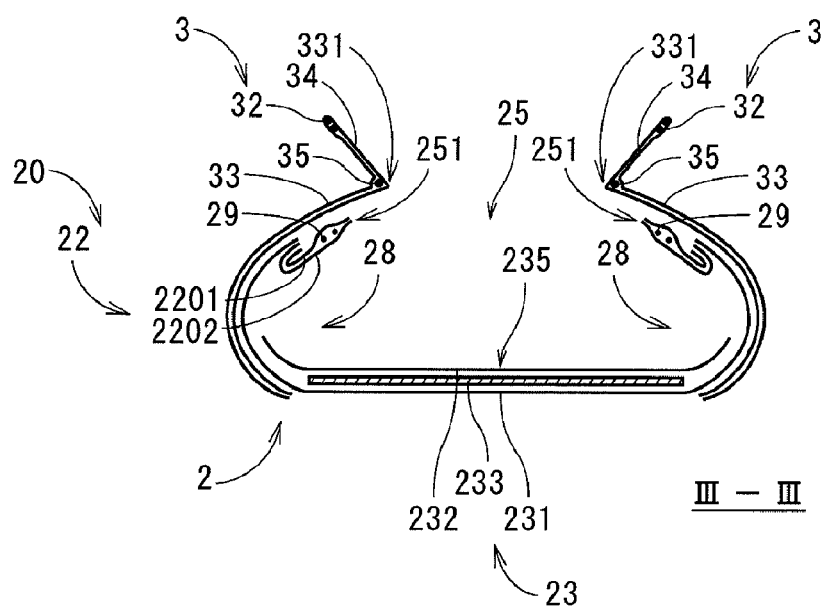
Figure 4:
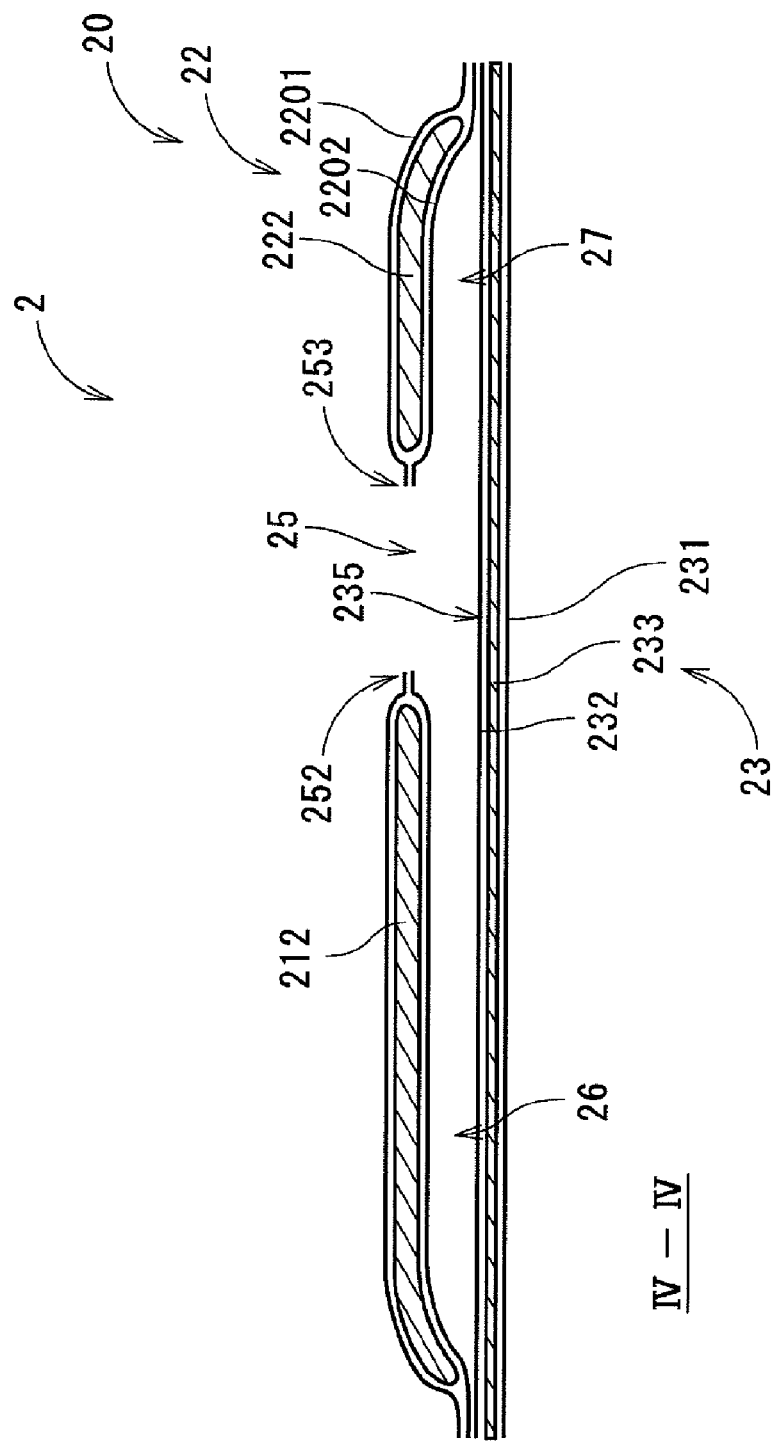

FIG. 2 is a cross-sectional view of the absorbent product 1 by a plane perpendicular to the longitudinal direction (i.e., the vertical direction of FIG. 1) of the absorbent product 1 at the positions indicated by arrows II-II of the front part 201 shown in FIG. 1, and FIG. 3 is a cross-sectional view of the absorbent product 1 by a plane perpendicular to the longitudinal direction at the positions indicated by arrows III-III of the middle part 202. FIG. 4 is a cross-sectional view of the absorbent product 1 by a plane perpendicular to the width direction of the absorbent product 1 at the positions indicated by arrows IV-IV shown in FIG. 1. The constitution of the rear part 203 is almost the same as that of the front part 201, and a cross-sectional view of the rear part 203 by a plane perpendicular to the longitudinal direction is the same as that in FIG. 2 in the absorbent product 1.

As shown in FIGS. 1 to 4, the main body part 2 has a back sheet 23 and the absorbent sheet member 20 which is overlapped on the back sheet 23 (i.e., overlapped on a side of the back sheet 23 toward the wearer) and is bonded to the back sheet 23 in the peripheral edges. The absorbent sheet member 20 has an opening 25 which is provided in a lower portion than the center with respect to the longitudinal direction of FIG. 1 and is to come into contact with the crotch region of the wearer. The width of the opening 25 is made smaller than that of the absorbent product 1. The back sheet 23 has a central exposed area 235 which is exposed in the opening 25 of the absorbent sheet member 20 and is directly to come into contact with the crotch region of the wearer.

As shown in FIGS. 1 and 4, the absorbent sheet member 20 has a front absorbent core 212 to be positioned on the front side (stomach side) of the wearer in wearing the absorbent product 1, a rear absorbent core 222 which is apart from the front absorbent core 212 in the longitudinal direction and is to be positioned on the back side of the wearer, and a liquid-pervious core covering sheet 22 for covering upper surfaces and lower surfaces of the front absorbent core 212 and the rear absorbent core 222 (i.e., surfaces of the front absorbent core 212 and the rear absorbent core 222 toward the wearer and surfaces of the front absorbent core 212 and the rear absorbent core 222 toward the back sheet 23). In the absorbent sheet member 20, the front absorbent core 212 is longer than the rear absorbent core 222 in the longitudinal direction, and the length of the front absorbent core 212 is approximately equal to twice or more than twice that of the rear absorbent core 222 in the preferred embodiment. The contours of the front absorbent core 212 and the rear absorbent core 222 are drawn by thick broken lines in FIG. 1.

As shown in FIGS. 2 and 4, the core covering sheet 22 has a first covering sheet 2201 for covering upper surfaces of the front absorbent core 212 and the rear absorbent core 222 and a second covering sheet 2202 for covering lower surfaces of the front absorbent core 212 and the rear absorbent core 222. The above-described opening 25 is provided between the front absorbent core 212 and the rear absorbent core 222 in the core covering sheet 22, and a portion for covering the front absorbent core 212 of the core covering sheet 22 and a portion for covering the rear absorbent core 222 are continuous on the both sides in the width direction of the opening 25.

As shown in FIG. 1, a core edge 2121 of the front absorbent core 212 toward (i.e., along) the opening 25 and a front edge 252 of the opening 25 toward (i.e., along) the front absorbent core 212 are both concave with respect to the longitudinal direction, and a core edge 2221 of the rear absorbent core 222 toward the opening 25 and a rear edge 253 of the opening 25 toward the rear absorbent core 222 are also both concave with respect to the longitudinal direction.

As shown in FIGS. 1 and 2, the front absorbent core 212 has a slit weakened line 241a which is located in the center with respect to the width direction of the absorbent sheet member 20, extending approximately along the longitudinal direction from the core edge 2121 (only shown in FIG. 1) located close to the opening 25. Similarly to the front absorbent core 212, the rear absorbent core 222 has a slit weakened line 242a which is located in the center with respect to the width direction of the absorbent sheet member 20, extending approximately along the longitudinal direction from the core edge 2221 located close to the opening 25, as shown in FIG. 1. The rigidity of the weakened line 241a is made lower than that of a portion excluding the weakened line 241a of the front absorbent core 212, and also the rigidity of the weakened line 242a is made lower than that of a portion excluding the weakened line 242a of the rear absorbent core 222. The weakened lines 241a, 242a are longer than halves of the front absorbent core 212 and the rear absorbent core 222 in the longitudinal direction, respectively. The contours of the weakened lines 241a, 242a are drawn by broken lines in FIG. 1.

In a case where the core edge 2121 of the front absorbent core 212 coincides with the front edge 252 of the opening 25 in plan view, the weakened line 241a extends approximately along the longitudinal direction from the core edge 2121 of the front absorbent core 212, the core edge 2121 being in contact with the opening 25. In a case where the core edge 2221 of the rear absorbent core 222 coincides with the rear edge 253 of the opening 25 in plan view, the weakened line 242a extends approximately along the longitudinal direction from the core edge 2221 of the rear absorbent core 222, the core edge 2221 being in contact with the opening 25.

The absorbent sheet member 20 has a pair of first elastic members 29 extending in the longitudinal direction on the both sides in the width direction of the opening 25 (i.e., the pair of first elastic members 29 are arranged along the arrangement direction of the front absorbent core 212 and the rear absorbent core 222, on the outsides in the width direction of the opening 25), as shown in FIGS. 1 and 3. As the first elastic members 29, polyurethane yarns, strip-like polyurethane films, yarn-like or strip-like natural rubber or the like are used for example. Each first elastic members 29 have two polyurethane yarns in the preferred embodiment.

As shown in FIG. 1, the first elastic members 29 extend in the longitudinal direction from positions where the first elastic members 29 overlay with the front absorbent core 212 to positions where they overlay with the rear absorbent core 222, at outward positions of the side edges 251 of the opening 25 (i.e., outward positions in the width direction of the side edges 251). As shown in FIG. 2, portions of the first elastic members 29 overlaying with the front absorbent core 212 are located between the front absorbent core 212 and the second covering sheet 2202 of the core covering sheet 22 under the front absorbent core 212 (i.e., on a side of the front absorbent core 212 toward the back sheet 23), and the extended first elastic members 29 are bonded to the second covering sheet 2202 and the front absorbent core 212. Portions of the first elastic members 29 overlaying with the rear absorbent core 222 are located between the rear absorbent core 222 and the second covering sheet 2202 under the rear absorbent core 222, and the extended first elastic members 29 are bonded to the second covering sheet 2202 and the rear absorbent core 222, similarly to the portions of the first elastic members 29 overlaying with the front absorbent core 212.

As shown in FIG. 3, portions of the first elastic members 29 between the front absorbent core 212 and the rear absorbent core 222 are located in the vicinity of the opening 25 between the first covering sheet 2201 and the second covering sheet 2202 of the core covering sheet 22, and the extended first elastic members 29 are bonded to the first covering sheet 2201 and the second covering sheet 2202. As discussed above, since the front absorbent core 212 and the rear absorbent core 222 are apart from each other with respect to the longitudinal direction, the front absorbent core 212 and the rear absorbent core 222 do not exist in both side areas in the width direction of the opening 25 (the both side areas include outside areas in the width direction of the pair of first elastic members 29).

In the vicinity of both end portions in the longitudinal direction of the main body part 2, the width of the front absorbent core 212 is made almost equal to that of the main body part 2, and the width of the rear absorbent core 222 is made almost equal to that of the main body part 2, as shown in FIG. 1. In portions around the opening 25 of the front absorbent core 212, the width of the front absorbent core 212 is gradually decreased in a direction toward the opening 25 and the rear absorbent core 222 in the absorbent sheet member 20. In portions around the opening 25 of the rear absorbent core 222, the width of the rear absorbent core 222 is gradually decreased in a direction toward the opening 25 and the front absorbent core 212. The pair of first elastic members 29 are located at outward positions of the front absorbent core 212 and the rear absorbent core 222 in the vicinity of the opening 25.

The front absorbent core 212 and the rear absorbent core 222 are formed by wrapping a mixture of hydrophilic fibers (e.g., crushed pulp fibers or cellulose fibers) and granulated absorbent polymers (e.g., SAP (Super Absorbent Polymer)) in a tissue paper, a liquid-pervious nonwoven fabric or the like, and the front absorbent core 212 and the rear absorbent core 222 rapidly absorb and retain the moisture which has passed through the core covering sheet 22. The tissue paper, the liquid-pervious nonwoven fabric or the like is bonded to the hydrophilic fibers and the absorbent polymers with hot melt adhesive, to prevent deformation of the hydrophilic fibers and falling of the absorbent polymers (especially, falling after absorption of moisture).

The first covering sheet 2201 and the second covering sheet 2202 of the core covering sheet 22 are nonwoven fabrics made of liquid-pervious sheet material, for example, hydrophilic fiber, and the first covering sheet 2201 and the second covering sheet 2202 immediately catch moisture of excrement from the wearer and move the moisture into the front absorbent core 212 and the rear absorbent core 222. Examples of nonwoven fabric used for the core covering sheet 22 are a point-bond nonwoven fabric, air-through nonwoven fabric, or spunlace nonwoven fabric, and as hydrophilic fibers for making these nonwoven fabrics, normally, cellulose, rayon, cotton or the like are used. As the core covering sheet 22, a liquid-pervious nonwoven fabric made of hydrophobic fiber (for example, polypropylene, polyethylene, polyester, polyamide, or nylon) with hydrophilic treatment using a surfactant may be utilized.

As shown in FIGS. 2 and 3, the back sheet 23 is bent toward the wearer on the both sides in the width direction of the main body part 2, and bonded to both end portions outside the pair of first elastic members 29 of the core covering sheet 22 by using the hot melt adhesive or the like so that the back sheet 23 covers both end portions of the front absorbent core 212 and the rear absorbent core 222.

As shown in FIG. 3, a surface of the core covering sheet 22 which faces the back sheet 23 directly (i.e., the surface of the core covering sheet 22 which faces the back sheet 23 without an intervening object), is not bonded to the back sheet 23 either on the both sides in the width direction of the opening 25 and at outsides of the pair of first elastic members 29 in the absorbent product 1. With this structure, a pair of side pockets 28 are formed between the core covering sheet 22 and the back sheet 23 on the both sides in the width direction of the opening 25.

The back sheet 23 has a water-repellent or liquid-impervious outer covering sheet 231, a very thin absorbent sheet 233 provided on the outer covering sheet 231 (i.e., provided on a side of the outer covering sheet 231 toward the wearer), and a hydrophilic sheet 232 which is laminated on the outer covering sheet 231 and the absorbent sheet 233 (i.e., laminated on a side of the outer covering sheet 231 and the absorbent sheet 233 toward the wearer). In other words, the absorbent sheet 233 is provided on a surface of the outer covering sheet 231, the surface being opposed to the absorbent sheet member 20, and the hydrophilic sheet 232 is laminated on the surface of the outer covering sheet 231.

As the outer covering sheet 231, used are water-repellent or liquid-impervious nonwoven fabric (i.e., spunbond nonwoven fabric, meltblown nonwoven fabric, or SMS (spunbond-meltblown-spunbond) nonwoven fabric) made of hydrophobic fiber (e.g., polypropylene, polyethylene, polyester, polyamide, or nylon), a water-repellent or liquid-impervious plastic film, or a laminated sheet of the water-repellent or liquid-impervious nonwoven fabric and the plastic film. The outer covering sheet 231 prevents moisture of excrement or the like from leaking out to the outside of the main body part 2. In a case where a plastic film is used for the outer covering sheet 231, it is preferable that a plastic film with permeability (breathability) is used as the outer covering sheet 231, from the view point of preventing sweatiness in the absorbent product 1 and providing comfortable feeling to the wearer.

The absorbent sheet 233 has two sheets and a high absorbent resin layer sandwiched between the two sheets. The high absorbent resin layer is formed by fixing granulated absorbent polymers such as the SAP between the two sheets by using the hot melt adhesive. Examples of the two sheets include a nonwoven fabric made of hydrophilic fibers, a nonwoven fabric made of hydrophobic fiber with hydrophilic treatment, a tissue paper, or the like. The high absorbent resin layer (i.e., the granulated absorbent polymers) is located between the above two sheets in strip form extending in the longitudinal direction. In other words, an area in which no absorbent polymers exist is provided between two linearly layer elements of the high absorbent resin layer, the layer elements extending in the longitudinal direction. The two sheets are bonded to each other in the areas in which no absorbent polymers exist, and each of the layer elements is sealed.

Instead of the absorbent sheet 233, there may be a case where the granulated absorbent polymers such as the SAP are applied onto the outer covering sheet 231, the absorbent polymers are bonded to the outer covering sheet 231 by the hot melt adhesive or the like, and thereby the high absorbent resin layer is directly formed on the outer covering sheet 231. Examples of the hydrophilic sheet 232 preferably include a nonwoven fabric made of hydrophilic fibers such as cellulose, rayon, or cotton (e.g., spunlace nonwoven fabric) or a hydrophilic nonwoven fabric made of hydrophobic fibers (e.g., polypropylene, polyethylene, polyester, polyamide, or nylon) with hydrophilic treatment using a surfactant.

Out of an outer portion of the front absorbent core 212 of the absorbent sheet member 20 shown in FIG. 1, a portion around the opening 25 (i.e., a portion around the opening 25 including outside areas of the pair of first elastic members 29), is not bonded to the upper surface of the back sheet 23 in the main body part 2 as shown in FIG. 4. The above portion can be explained in the preferred embodiment as a portion which includes the front edge 252 of the opening 25 and portions from the front edge 252 approximately to both ends in the width direction of the main body part 2, out of the outer portion of the front absorbent core 212. Out of the outer portion of the front absorbent core 212, a portion excluding both of the opening 25 which is the above portion without being bonded to the back sheet 23 and a portion around the opening 25, are bonded to the back sheet 23 as shown in FIG. 2, to form a front pocket 26 between the front absorbent core 212 and the back sheet 23 (i.e., between a portion of the absorbent sheet member 20 corresponding to the front absorbent core 212 and the back sheet 23).

Out of an outer portion of the rear absorbent core 222 of the absorbent sheet member 20 shown in FIG. 1, a portion around the opening 25 (i.e., a portion around the opening 25 including outside areas of the pair of first elastic members 29), is not bonded to the upper surface of the back sheet 23 in the main body part 2 (see FIG. 4). The above portion can be explained in the preferred embodiment as a portion which includes the rear edge 253 of the opening 25 and portions from the rear edge 253 approximately to both ends in the width direction of the main body part 2, out of the outer portion of the rear absorbent core 222. Out of the outer portion of the rear absorbent core 222, a portion which excludes both of the opening 25 which is the above portion without being bonded to the back sheet 23 and a portion around the opening 25, are bonded to the back sheet 23, to form a rear pocket 27 between the rear absorbent core 222 and the back sheet 23 (i.e., between a portion of the absorbent sheet member 20 corresponding to the rear absorbent core 222 and the back sheet 23). In the absorbent product 1 shown in FIG. 1, the front pocket 26 and the rear pocket 27 are continuous with the pair of side pockets 28.

In the absorbent product 1 shown in FIGS. 1 to 4, excrement such as loose stool discharged from the wearer reaches the back sheet 23 through the opening 25 to be received by the central exposed area 235 of the back sheet 23. The excrement received by the central exposed area 235 moves to internal spaces of the front pocket 26, the side pockets 28 and the rear pocket 27 to be kept therein.

Each of the pair of side sheets 3 shown in FIGS. 1 to 3 is formed by bonding extended elastic members in the longitudinal direction between two layers of a strip member, the two layers being made by folding one sheet member into two (that is to say, each side sheet 3 has a two-layer structure). Each side sheet 3 has a bonded part 33 which is a strip-like portion bonded on the core covering sheet 22 and the back sheet 23, a side wall part 34, at least part of the side wall part 34 standing up from an inner edge 331 of the bonded part 33, second elastic members 32 which are bonded to an upper end portion of the side wall part 34 (i.e., an end portion of the side wall part 34 toward the wearer) in the longitudinal direction (that is, the second elastic members 32 are arranged and bonded along the longitudinal direction), and a third elastic member 35 which is bonded to the inner edge 331 of the bonded part 33 in the longitudinal direction.

As the bonded part 33 and the side wall part 34, employed are water-repellent or liquid-impervious nonwoven fabric (i.e., spunbond nonwoven fabric, meltblown nonwoven fabric, or SMS nonwoven fabric) made of hydrophobic fiber (e.g., polypropylene, polyethylene, polyester, polyamide, or nylon). As the second elastic members 32 and the third elastic member 35, polyurethane yarn, strip-like polyurethane film, yarn-like or strip-like natural rubber, or the like are used for example. In the preferred embodiment, the second elastic members 32 have two polyurethane yarns, and the third elastic member 35 has one polyurethane yarn.

As shown in FIGS. 2 and 3, each bonded part 33 bonded on the upper surface of the core covering sheet 22 (i.e., bonded on a surface of the core covering sheet 22 toward the wearer) covers a portion of the back sheet 23 on the outside of the core covering sheet 22, the portion covering a side end portion of the absorbent sheet member 20, and the bonded part 33 is continuous with a side end portion of the back sheet 23 opposed to the wearer, and bonded on the back sheet 23 by the hot melt adhesive or the like. As described above, since both side portions of the main body part 2 are covered with the water-repellent or liquid-impervious side sheets 3, even if there exists any poor bonding between the absorbent sheet member 20 and the back sheet 23 in the both side portions of the main body part 2, it is possible to surely prevent excrement kept in internal spaces of the front pocket 26, the side pockets 28 and the rear pocket 27 from leaking out of a portion of poor bonding to the outside. Further, since the side sheets 3 have the two-layer structure, it is possible to prevent leakage of the excrement to the outside more reliably.

As shown in FIGS. 1 and 3, the inner edge 331 of the bonded part 33 (i.e., the border between the bonded part 33 and the side wall part 34) is located in the inside of the side edge 251 (i.e., the inside in the width direction of the side edge 251) of the opening 25 in the absorbent sheet member 20, and a space in the vicinity of the side edge 251 of the opening 25 is covered with the bonded part 33. With this structure, the third elastic member 35 bonded to the inner edge 331 of the bonded part 33 is located across the opening 25 in the longitudinal direction.

Figure 5:
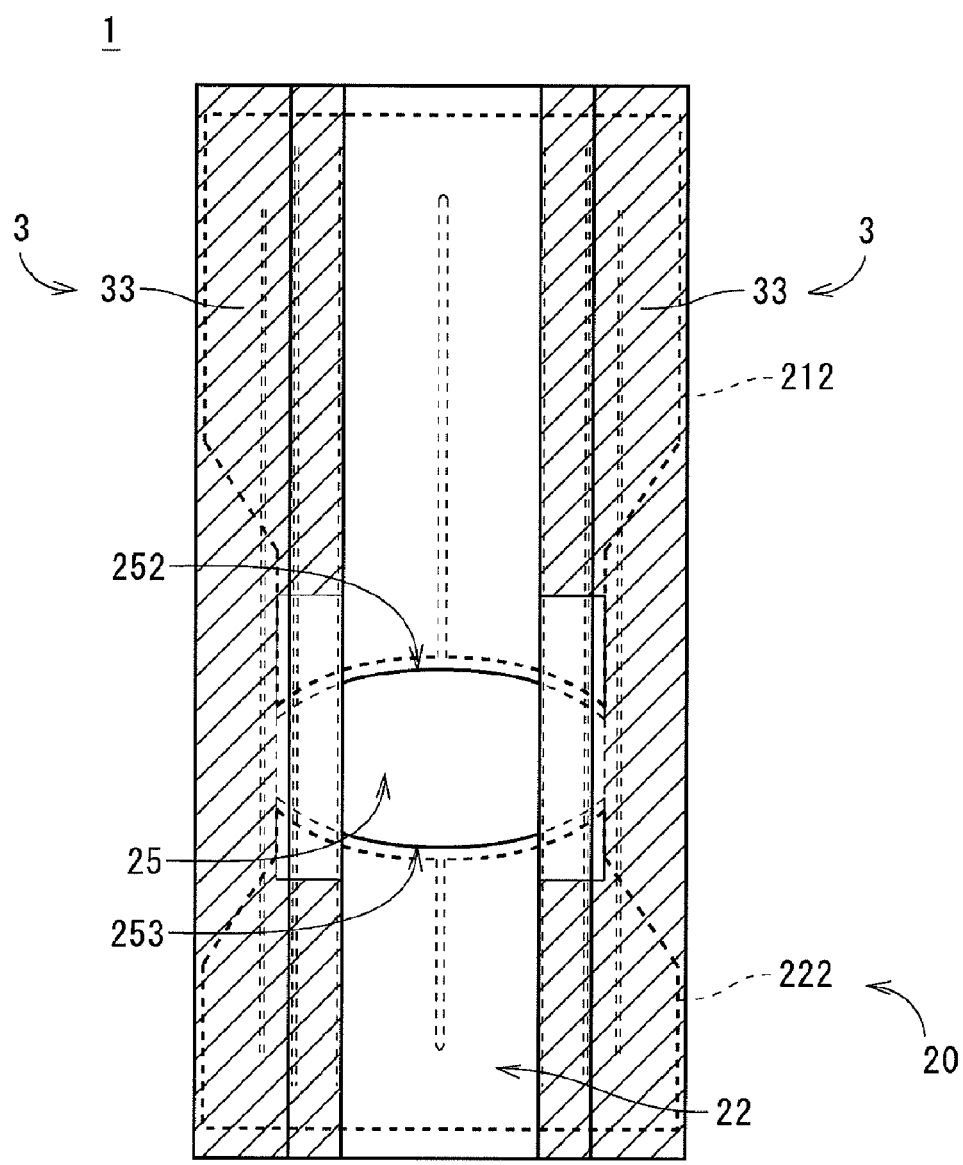
FIG. 5 is a plan view of the absorbent product.

FIG. 5 is a plan view showing the expanded absorbent product 1 similarly to FIG. 1. Out of the bonded part 33 in each side sheet 3, a portion which is actually bonded on the core covering sheet 20 (an actually bonded portion of the bonded part 33) with the hot melt adhesive or the like is assigned hatching lines in FIG. 5. A portion within a predetermined distance (e.g., about 2 cm) from the front edge 252 of the opening 25 toward the front side of the absorbent product 1 (i.e., toward a direction apart from the opening 25 in the longitudinal direction) and a portion within a predetermined distance (e.g., about 2 cm) from the rear edge 253 of the opening 25 toward the back side, are not bonded with the core covering sheet 22 in the absorbent sheet member 20, as shown in FIG. 5. In other words, the bonded part 33 in each side sheet 3 is not bonded with the core covering sheet 22 in the vicinity of the front edge 252 of the opening 25 above the front absorbent core 212, and also not bonded with the core covering sheet 22 in the vicinity of the rear edge 253 of the opening 25 above the rear absorbent core 222.

Each side sheet 3 is bent outwardly and toward the wearer from the inner edge 331 of the bonded part 33 as shown in FIGS. 2 and 3, and both end portions in the longitudinal direction of the side wall part 34 which is a bent portion are fixed on the bonded part 33 by the hot melt adhesive or the like. In the absorbent product 1, portions between the both end portions in the longitudinal direction (i.e., portions fixed on the bonded part 33) of the side wall parts 34 stand up outwardly and toward the wearer from the inner edges 331 of the bonded parts 33 by contraction of the extended second elastic members 32 bonded on the side wall parts 34, to form standing gathers which come into contact with the vicinity of wearer's crotch in wearing.

In each of the pair of side sheets 3, the front absorbent core 212 and the rear absorbent core 222 are drawn toward each other by contraction of the extended third elastic member 35 which is bonded on the inner edge 331 of the bonded part 33 across the opening 25 in the absorbent product 1. Therefore, the front absorbent core 212 and the rear absorbent core 222 are raised toward the wearer so that they should become apart from the back sheet 23 (i.e., so that the distance in the thickness direction between the front absorbent core 212 and the back sheet 23 in the front pocket 26 and the distance in the thickness direction between the rear absorbent core 222 and the back sheet 23 in the rear pocket 27 should become larger).

With this structure, it is possible to keep the distance larger in the thickness direction between the absorbent sheet member 20 and the back sheet 23 in the vicinity of the opening 25 and to fit a portion around the opening 25 of the absorbent sheet member 20 to the wearer. As a result, it is possible to surely keep and retain the excrement in the front pocket 26, the side pockets 28, and the rear pocket 27, and to prevent expansion and wide adhesion of the excrement to the wearer. As described above, since the absorbent product 1 can prevent wide expansion of the excrement, it is especially suitable for an auxiliary absorbent pad which covers a relatively narrow range of the crotch region on the inner side of an exterior product such as a disposal diaper, to be easily exchangeable.

The pair of extended first elastic members 29 bonded with the core covering sheet 22 on the both sides (i.e., on the outsides in the width direction) of the opening 25 are provided in the absorbent sheet member 20, and the core covering sheet 22 in the absorbent sheet member 20 greatly stands up toward the wearer together with the back sheet 23 in each of the pair of side pockets 28, by contraction of the first elastic members 29 in the longitudinal direction as shown in FIG. 3. As a result, the heights of the side pockets 28 can be increased.

The front absorbent core 212 and the rear absorbent core 222 are drawn toward each other by contraction of the first elastic members 29, and the front absorbent core 212 and the rear absorbent core 222 are raised toward the wearer so that they should become apart from the back sheet 23, as shown in FIGS. 2 and 4. With this structure, it is possible to increase the distance in the thickness direction between the absorbent sheet member 20 and the back sheet 23 in the vicinity of the opening 25 and to fit a portion around the opening 25 of the absorbent sheet member 20 to the wearer. As a result, it is possible to surely keep and retain the excrement in the front pocket 26, the side pockets 28, and the rear pocket 27, and to prevent expansion and wide adhesion of the excrement to the wearer.

As discussed above, the bonded part 33 in each side sheet 3 is not bonded with the core covering sheet 22 in the vicinity of the front edge 252 of the opening 25 above the front absorbent core 212, and is not bonded with the core covering sheet 22 in the vicinity of the rear edge 253 of the opening 25 above the rear absorbent core 222 in the absorbent product 1. With this structure, the front absorbent core 212 and the rear absorbent core 222 are easily deformable in the vicinity of the opening 25, independently of the side sheets 3, and the front absorbent core 212 and the rear absorbent core 222 can be convexly deformed toward a direction apart from the back sheet 23 easily, by contraction of the third elastic members 35 and the first elastic members 29. As a result, it is possible to further increase the distance in the thickness direction between the absorbent sheet member 20 and the back sheet 23 in the vicinity of the opening 25 and to fit a portion around the opening 25 of the absorbent sheet member 20 to the wearer securely.

As discussed above, the weakened line 241a located in the center with respect to the width direction of the front absorbent core 212 (i.e., the center with respect to the width direction of the absorbent sheet member 20), the weakened line 241a extending approximately along the longitudinal direction from the core edge 2121, is formed in the absorbent sheet member 20. The weakened line 242a located in the center with respect to the width direction of the rear absorbent core 222, the weakened line 242a extending approximately along the longitudinal direction from the core edge 2221, is further formed in the absorbent sheet member 20. The front absorbent core 212 is bent at the weakened line 241a in wearing the absorbent product 1 to thereby form a projected part 240 projecting toward the direction apart from the back sheet 23 (i.e., toward the wearer) in the center with respect to the width direction of the front absorbent core 212, as shown in FIG. 2. Further, the rear absorbent core 222 is bent at the weakened line 242a in wearing the absorbent product 1 to thereby form a projected part projecting toward the direction apart from the back sheet 23 in the center with respect to the width direction of the rear absorbent core 222. As a result, it is possible to enhance fitting of a portion around the opening 25 of the absorbent sheet member 20 to the wearer.

In the absorbent sheet member 20, since the weakened line 241a is a slit extending in the longitudinal direction, it is possible to easily form the weakened line 241a. Similarly, since the weakened line 242a is a slit extending in the longitudinal direction, the weakened line 242a can be easily formed.

In the absorbent product 1, excrement such as urine which is discharged around the opening 25 without being kept in the front pocket 26, the side pockets 28 and the rear pocket 27 through the opening 25, can be prevented from leaking out of the sides of the absorbent product 1 (so-called side leakage can be prevented) by providing the pair of side wall parts 34 standing up toward the wearer. Since each side wall part 34 stands up toward the outside from the inner edge 331 of the bonded part 33, the stability of the shape of the side wall part 34 is improved and the side wall part 34 easily fits the wearer, to thereby prevent the side leakage of excrement more reliably.

In the above preferred embodiment, although the third elastic member 35 in each side sheet 3 is bonded on the inner edge 331 of the bonded part 33, the inner edge 331 being the border between the bonded part 33 and the side wall part 34, the third elastic member 35 may be bonded on the bonded part 33 inner than the side edge 251 of the opening 25 or bonded on the side wall part 34 in the vicinity of the bonded part 33 (i.e., in the vicinity of the inner edge 331). By contraction of the third elastic members 35 bonded by the above manner, the front absorbent core 212 and the rear absorbent core 222 are drawn toward each other, and the front absorbent core 212 and the rear absorbent core 222 are raised toward the wearer so that they should become apart from the back sheet 23, similarly to the above case. As a result, it is possible to keep the distance larger in the thickness direction between the absorbent sheet member 20 and the back sheet 23 in the vicinity of the opening 25 and to fit a portion around the opening 25 of the absorbent sheet member 20 to the wearer.

In order to raise the front absorbent core 212 and the rear absorbent core 222 toward the wearer to be largely apart from the back sheet 23, it is preferred that the third elastic member 35 in each side sheet 3 is bonded either on the bonded part 33 or on the side wall part 34 in the vicinity of the inner edge 331 of the bonded part 33 in the absorbent product 1. In this manner, the front absorbent core 212 and the rear absorbent core 222 are drawn toward each other in the longitudinal direction at positions which are away in the width direction from portions fixed on the back sheet 23 of the both absorbent cores (i.e., the portions are side edges of the both absorbent cores), and it is therefore possible to further increase the distance in the thickness direction between the absorbent sheet member 20 and the back sheet 23 in the vicinity of the opening 25 and to fit a portion around the opening 25 of the absorbent sheet member 20 to the wearer securely.

Though the preferred embodiment of the present invention has been discussed above, the present invention is not limited to the above-discussed preferred embodiment, but allows various variations.

In the absorbent product 1, it is preferred that both of the front pocket 26 and the rear pocket 27 are provided between the absorbent sheet member 20 and the back sheet 23 to surely prevent wide adhesion of excrement to a wearer by increasing the capacity of a pocket which keeps excrement. However, even if a pocket is provided between one absorbent core out of the front absorbent core 212 and the rear absorbent core 222 and the back sheet 23 and no pocket is provided between the other absorbent core and the back sheet 23 (in this case, a portion corresponding to the other absorbent core in the absorbent sheet member 20 is bonded on the back sheet 23 across almost the whole surface), one absorbent core is drawn toward the other absorbent core by contraction of the third elastic member 35 in each side sheet 3 and it is thereby possible to keep the distance larger in the thickness direction between the absorbent sheet member 20 and the back sheet 23 in the vicinity of the opening 25 and to fit a portion around the opening 25 of the absorbent sheet member 20 to the wearer. Consequently, the wide adhesion of excrement to the wearer is prevented.

As described above, in the case that a pocket is provided between one absorbent core and the back sheet 23 and no pocket is provided between the other absorbent core and the back sheet 23, it is preferable that the front absorbent core 212 serves as the one absorbent core and the front pocket 26 is formed between the front absorbent core 212 and the back sheet 23, and the front absorbent core 212 is made longer than the rear absorbent core 222 in the longitudinal direction. With this structure, it is possible to accurately keep excrement from a wearer in the front pocket 26, such as sleeping face up on a bed, and to prevent wide adhesion of the excrement to the wearer.

In order to increase the distance in the thickness direction between the absorbent sheet member 20 and the back sheet 23 in the vicinity of the opening 25 and to fit a portion around the opening 25 of the absorbent sheet member 20 to the wearer, it is preferable that the bonded part 33 in each side sheet 3 is not bonded with the core covering sheet 22 in the vicinity of the opening 25 above both of the front absorbent core 212 and the rear absorbent core 222, but it is not necessary that the bonded part 33 is not bonded with the core covering sheet 22 above the both absorbent cores. For example, in a case where the front pocket 26 and the rear pocket 27 are provided between the front absorbent core 212 and the rear absorbent core 222 and the back skeet 23 similarly to the above preferred embodiment, the bonded part 33 is not bonded with the core covering sheet 22 in the vicinity of the opening 25 above one absorbent core out of the front absorbent core 212 and the rear absorbent core 222, and it is thereby possible to increase the distance in the thickness direction between the one absorbent core and the back sheet 23 and to fit a portion around the opening 25 of the one absorbent core to the wearer. In a case where a pocket is provided between one absorbent core out of the front absorbent core 212 and the rear absorbent core 222 and the back sheet 23 and no pocket is provided between the other absorbent core and the back sheet 23, the bonded part 33 is not bonded with the core covering sheet 22 in the vicinity of the opening 25 above the one absorbent core.

From the viewpoint of increasing the distance in the thickness direction between the absorbent sheet member 20 and the back sheet 23 in the vicinity of the opening 25 and fitting a portion around the opening 25 of the absorbent sheet member 20 to the wearer, it is preferable that the first elastic members 29 extend from positions where they overlay with the front absorbent core 212 to positions where they overlay with the rear absorbent core 222, but are not required to extend from positions where they overlay with the front absorbent core 212 to positions where they overlay with the rear absorbent core 222. For instance, in the case that the front pocket 26 and the rear pocket 27 are provided as described above, the first elastic members 29 have only to extend at least from outward positions of the both side edges 251 of the opening 25 to positions where the first elastic members 29 overlay with one absorbent core out of the front absorbent core 212 and the rear absorbent core 222.

In the case that a pocket is formed between one absorbent core out of the front absorbent core 212 and the rear absorbent core 222 and the back sheet 23 and no pocket is formed between the other absorbent core and the back sheet 23, the first elastic members 29 extend from outward positions of the both side edges 251 of the opening 25 to positions where the first elastic members 29 overlay with the one absorbent core. The first elastic members 29 have only to be bonded with the core covering sheet 22, e.g., may be bonded between the front absorbent core 212 and the rear absorbent core 222 and the first covering sheet 2201 of the core covering sheet 22 above the both absorbent cores (on the side toward the wearer).

In the absorbent product 1 according to the above preferred embodiment, there may be a case where a plurality of weakened lines are provided in the front absorbent core 212 instead of one weakened line 241$a$, and a plurality of weakened lines are provided in the rear absorbent core 222 instead of one weakened line 242$a$. In the following description, a plurality of weakened lines provided in each absorbent core are referred as a "weakened line group". In the case where only one weakened line is provided in the absorbent core like in the above preferred embodiment, one weakened line is also referred to as a "weakened line group".

Figure 6:
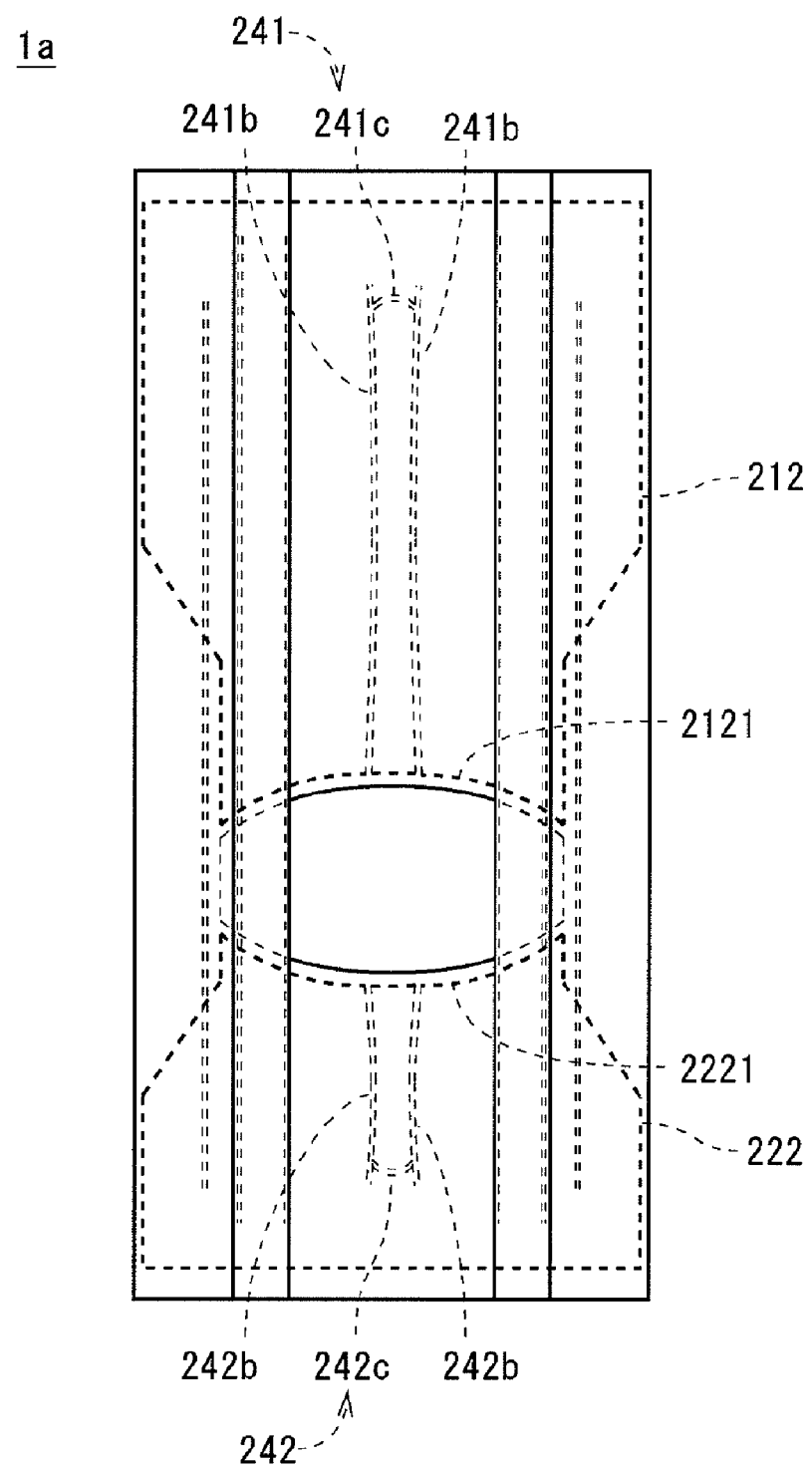
FIGS. 6 and 7 are plan views each showing another example of the absorbent product.
Figure 7:
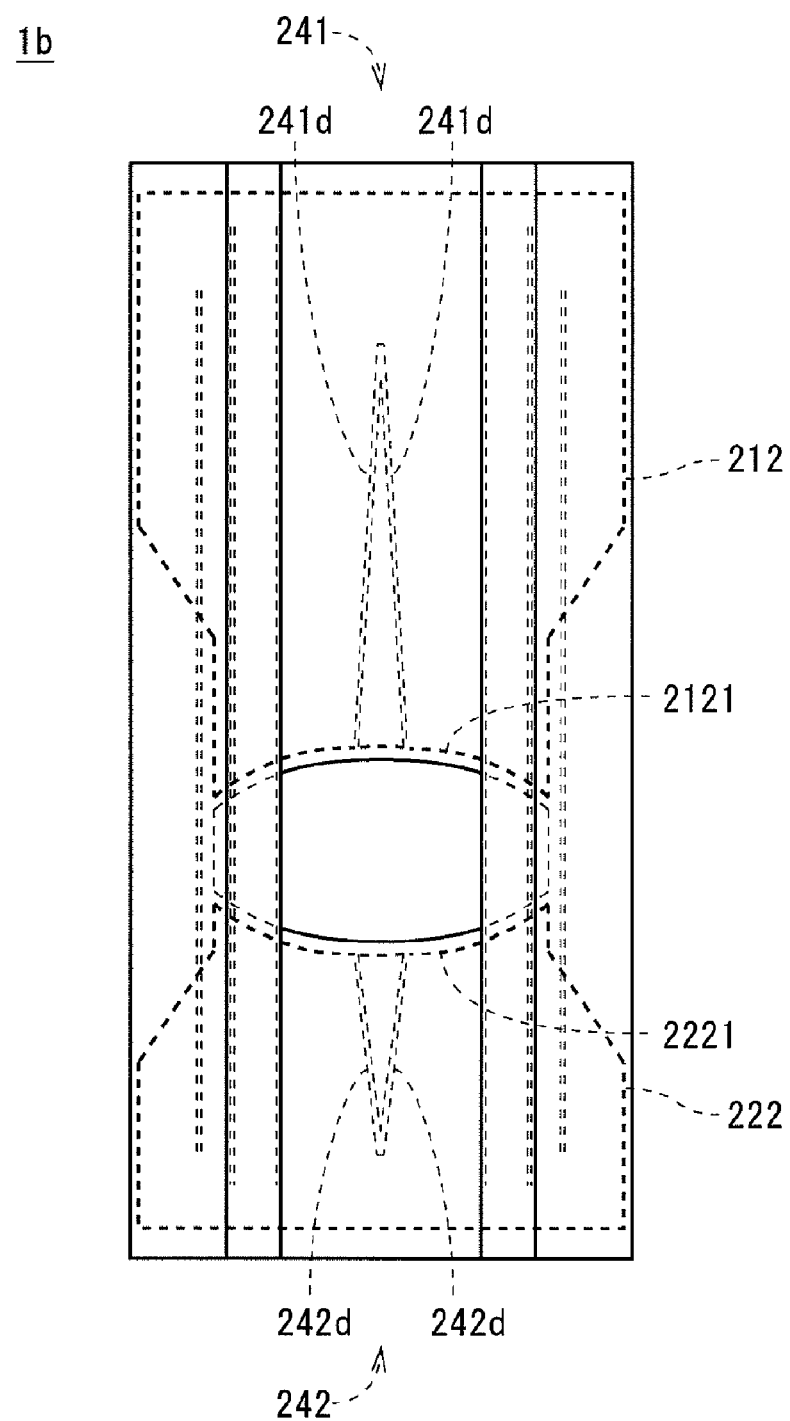

FIGS. 6 and 7 are plan views each showing an example of an absorbent product with a weakened line group including a plurality of weakened lines. In an absorbent product 1$a$ shown in FIG. 6, the front absorbent core 212 is provided with a weakened line group 241 having a pair of weakened lines 241$b$ which extend almost in parallel along the longitudinal direction from the core edge 2121 and an auxiliary weakened line 241$c$ extending approximately along the width direction between the pair of weakened lines 241$b$, at a position apart from the core edge 2121 in the longitudinal direction. The rear absorbent core 222 is provided with a weakened line group 242 having a pair of weakened lines 242$b$ which extend almost in parallel along the longitudinal direction from the core edge 2221 and an auxiliary weakened line 242$c$ extending approximately along the width direction between the pair of weakened lines 242$b$, at a position apart from the core edge 2221 in the longitudinal direction.

In an absorbent product 1$b$ shown in FIG. 7, the front absorbent core 212 is provided with a weakened line group 241 having a pair of weakened lines 241$d$ extending approximately along the longitudinal direction from the core edge 2121, and the distance in the width direction between the pair of weakened lines 241$d$ decreases as being away from the core edge 2121. The rear absorbent core 222 is provided with a weakened line group 242 having a pair of weakened lines 242$d$ extending approximately along the longitudinal direction from the core edge 2221, and the distance in the width direction between the pair of weakened lines 242$d$ decreases as being away from the core edge 2221.

Though it is preferred that the above weakened line group is provided with both of the front absorbent core 212 and the rear absorbent core 222 to enhance fitting of a portion around the opening 25 of the absorbent sheet member 20 to the wearer, the weakened line group is not required to be provided in the both absorbent cores. For example, in the case where the front pocket 26 and the rear pocket 27 are provided as discussed above, the weakened line group is provided in one absorbent core out of the front absorbent core 212 and the rear absorbent core 222 and therefore, it is possible to further fit a portion around the opening 25 of the one absorbent core to the wearer. In the case that a pocket is formed between one absorbent core out of the front absorbent core 212 and the rear absorbent core 222 and the back sheet 23 and no pocket is formed between the other absorbent core and the back sheet 23, the weakened line group is located in the one absorbent core.

A weakened line included in the weakened line group is not limited to a slit formed by cutting, e.g., may be formed by reducing the thicknesses of the front absorbent core 212 and the rear absorbent core 222 by embossing or may be formed by partially decreasing an amount of hydrophilic fibers making the front absorbent core 212 and the rear absorbent core 222 and reducing the thicknesses of the front absorbent core 212 and the rear absorbent core 222. However, since the weakened line which is a slit extending in the longitudinal direction is included in the weakened line group, the weakened line group can be easily formed.

The core covering sheet 22 may be one sheet member in the absorbent sheet member 20. In this case, a portion of the one sheet member for covering the upper surfaces of the front absorbent core 212 and the rear absorbent core 222 corresponds to the first covering sheet 2201, and a portion of the one sheet member for covering the lower surfaces of the front absorbent core 212 and the rear absorbent core 222 corresponds to the second covering sheet 2202. The core covering sheet 22 has only to cover at least the upper surfaces of the front absorbent core 212 and the rear absorbent core 222.

The structure of the absorbent product 1 may be applied to, e.g., a pants-type disposal diaper having a waist opening at an upper end and a pair of leg openings on a lower part or an open-type disposal diaper where a portion located on the front side of a wearer and a portion located on the back side are fastened around the waistline of the wearer in wearing the disposal diaper, as well as an auxiliary absorbent pad which is attached on (the inner side of) an exterior product.

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2008-288420 filed in the Japan Patent Office on Nov. 11, 2008, the entire disclosure of which is incorporated herein by reference.

What is claimed is:

1. An absorbent product for receiving excrement from a wearer, comprising:
a back sheet;
an absorbent sheet member which overlaps said back sheet, said absorbent sheet member having an opening to come into contact with a crotch region of a wearer; and
a pair of side sheets located on both side portions of said absorbent sheet member, each of said side sheets extending in a longitudinal direction of said absorbent sheet member,
wherein said absorbent sheet member comprises:
a front absorbent core to be positioned on a front side of the wearer;
a rear absorbent core to be positioned on a back side of the wearer; and
a liquid-pervious core covering sheet for covering said front absorbent core and said rear absorbent core, said core covering sheet having said opening between said front absorbent core and said rear absorbent core,
an outer portion of one absorbent core out of said front absorbent core and said rear absorbent core in said absorbent sheet member, excluding a portion around said opening, is bonded to said back sheet, to form a pocket between said one absorbent core and said back sheet, and
wherein each of said side sheets comprises:
a bonded part which is a strip portion bonded on said core covering sheet in the longitudinal direction, an inner edge of said bonded part being located in the inside of a side edge of said opening, said bonded part being not bonded with said core covering sheet in the vicinity of an edge of said opening above said one absorbent core;
a side wall part which is a bent portion bent outwardly and toward the wearer from said inner edge of said bonded part, at least part of said side wall part standing up from said inner edge of said bonded part; and
an elastic member which is bonded on said bonded part in the longitudinal direction on the inner side of said side edge of said opening, said elastic member extending across said opening, and said one absorbent core being drawn toward the other absorbent core by contraction of said elastic member.

2. The absorbent product according to claim 1, wherein said one absorbent core is said front absorbent core, and said front absorbent core is longer than said rear absorbent core in the longitudinal direction.

3. The absorbent product according to claim 1, wherein said side wall part stands up toward the outside from said inner edge of said bonded part.

4. The absorbent product according to claim 3, wherein said elastic member in each of said side sheet is bonded on the respective bonded part in the vicinity of said inner edge of said bonded part.

5. The absorbent product according to claim 2, wherein said absorbent sheet member further comprises other elastic members which are bonded on said core covering sheet and extend in said both side portions of said absorbent sheet member in the longitudinal direction, and
said other elastic members extend at least from outward positions of both side edges of said opening to positions where said other elastic members overlay with said one absorbent core, and said one absorbent core is drawn toward said other absorbent core by contraction of said other elastic members.

6. The absorbent product according to claim 5, wherein said one absorbent core has a weakened line group located in the center with respect to a width direction of said absorbent sheet member, said weakened line group extending approximately along the longitudinal direction from a core edge of said one absorbent core, said core edge being located close to said opening or in contact with said opening, and said one absorbent core is bent at said weakened line group, to form a projected part projecting toward the wearer.

7. The absorbent product according to claim 1, wherein said elastic member in each of said side sheet is bonded on the respective bonded part in the vicinity of said inner edge of said bonded part.

8. The absorbent product according to claim 1, wherein said absorbent sheet member further comprises other elastic members which are bonded on said core covering sheet and extend in said both side portions of said absorbent sheet member in the longitudinal direction, and
said other elastic members extend at least from outward positions of both side edges of said opening to positions where said other elastic members overlay with said one absorbent core, and said one absorbent core is drawn toward said other absorbent core by contraction of said other elastic members.

9. The absorbent product according to claim 8, wherein said one absorbent core has a weakened line group located in the center with respect to a width direction of said absorbent sheet member, said weakened line group extending approximately along the longitudinal direction from a core edge of said one absorbent core, said core edge being located close to said opening or in contact with said opening, and said one absorbent core is bent at said weakened line group, to form a projected part projecting toward the wearer.

10. The absorbent product according to claim 1, wherein said one absorbent core has a weakened line group located in the center with respect to a width direction of said absorbent sheet member, said weakened line group extending approximately along the longitudinal direction from a core edge of said one absorbent core, said core edge being located close to said opening or in contact with said opening, and said one absorbent core is bent at said weakened line group, to form a projected part projecting toward the wearer.

11. The absorbent product according to claim 1, wherein an outer portion of said other absorbent core out of said front absorbent core and said rear absorbent core in said absorbent sheet member, excluding a portion around said opening, is bonded to said back sheet, to form another pocket between said other absorbent core and said back sheet.

12. The absorbent product according to claim 11, wherein said other absorbent core has a weakened line group located in the center with respect to a width direction of said absorbent sheet member, said weakened line group extending approximately along the longitudinal direction from a core edge of said other absorbent core, said core edge being located close to said opening or in contact with said opening, and said other absorbent core is bent at said weakened line group, to form a projected part projecting toward the wearer.

13. The absorbent product according to claim 1, wherein said absorbent product is an auxiliary absorbent pad which is attached on an inner side of an exterior product worn by the wearer.

14. The absorbent product according to claim 11, wherein said bonding part is not bonded with said core covering sheet in the vicinity of an edge of said opening above said other absorbent core.

* * * * *